United States Patent [19]

Green

[11] Patent Number: 4,624,143

[45] Date of Patent: Nov. 25, 1986

[54] ULTRASONIC REFLEX TRANSMISSION IMAGING METHOD AND APPARATUS WITH EXTERNAL REFLECTOR

[75] Inventor: Philip S. Green, Atherton, Calif.

[73] Assignee: SRI International, Menlo Park, Calif.

[21] Appl. No.: 755,287

[22] Filed: Jul. 15, 1985

Related U.S. Application Data

[63] Continuation-in-part of Ser. No. 715,199, Mar. 22, 1985.

[51] Int. Cl.⁴ .............................................. G01N 29/00
[52] U.S. Cl. ........................................ 73/620; 128/660
[58] Field of Search ................ 73/620, 618, 627, 628, 73/631, 606, 607; 128/660

[56] References Cited

U.S. PATENT DOCUMENTS

| | | | |
|---|---|---|---|
| 3,937,066 | 2/1976 | Green et al. | 73/607 |
| 4,016,750 | 4/1977 | Green | 73/629 |
| 4,305,296 | 12/1981 | Green et al. | 73/626 |
| 4,457,175 | 7/1981 | Ramsey, Jr. et al. | 73/606 |

OTHER PUBLICATIONS

P. D. Edmonds et al., "A Human Abdominal Tissue Phantom", Ultrasonic Tissue Characterization II, M. Linzer, ed., Nat. Bureau of Standards, Spec. Publ. 525, pp. 323-326, (1977).

J. C. Macado, et al., "Acoustic Wave Propagation in Randomly Distributed Spherical Particles", J. Acoust. Soc. Amer., 74(5), Nov. 1983, pp. 1529-1534.

H. Kanda et al., "Acoustic Microscope Observation of a Biological Specimen in a Total Reflector Backing Configuration", Ultrasonic Imaging, 5, (1983), p. 1, Abstract.

Primary Examiner—Stephen A. Kreitman
Attorney, Agent, or Firm—Victor R. Beckman

[57] ABSTRACT

An ultrasonic imaging system and method are disclosed which include a transducer (10) for pulse insonification (16) of an object (14). Reflecting means (29) containing scatterers is acoustically coupled to object (14) opposite transducer (10). Echo signals received from within reflecting means (29) are converted to electrical signals at the transducer (10), which electrical signals are supplied to a signal processor (30) for processing the same. Echo signals obtained from a range zone (Z) within reflecting means (29) are integrated by integrator (42). The amplitude of echo signals from the range zone (Z) is strongly dependent upon attenuation at the focal point (F) whereby the integrator (42) output (60) also is strongly dependent upon attenuation at the focal point (F). The integrator (42) output (60) is supplied to a display (48) for use in establishing one pixel thereof. A C-scan display is provided by scanning the focal point (F) in a focal plane (22) substantially normal to the beam axis (20).

17 Claims, 3 Drawing Figures

ULTRASONIC REFLEX TRANSMISSION IMAGING METHOD AND APPARATUS WITH EXTERNAL REFLECTOR

RELATED APPLICATIONS

This is a continuation-in-part application of U.S. patent application Ser. No. 715,199 filed Mar. 22, 1985 by Philip S. Green entitled Ultrasonic Reflex Transmission Imaging Method and Apparatus.

FIELD OF THE INVENTION

This invention relates generally to an ultrasonic imaging method and apparatus which includes the use of external scatterers acoustically coupled to the object to be imaged, from which scatterers ultrasonic energy is reflected back through the object, for use in producing an image of the interior of the object.

BACKGROUND OF THE INVENTION

Ultrasonic imaging systems of the transmission type wherein a transmitting transducer and a receiving transducer are located at opposite sides of an object or specimen under examination are well known as shown, for example, in U.S. Pat. No. 3,937,066, Green et al and 4,457,175, Ramsey, Jr. et al. Generally C-scan images are provided by transmission type systems which lie in a plane normal to the transmitted waves. Echo type ultrasonic imaging systems also are well known as shown, for example, in U.S. Pat. Nos. 4,016,750, P. S. Green and 4,305,296, Green et al. Generally B-scan type images are produced by echo type systems wherein the image formed lies in a plane containing the propagated waves. Of course, C-scan images also may be obtained using echno techniques.

SUMMARY AND OBJECTS OF THE INVENTION

An object of this invention is the provision of an ultrasonic imaging system and method which combine features of echo and transmission type systems for improved imaging.

An object of this invention is the provision of an improved echo-transmission type ultrasonic imaging system and method wherein transmitted signals are reflected from scatterers in reflecting means acoustically coupled to the surface of the object opposite an ultrasonic probe.

In accordance with the present invention a transmitter energizes a transducer for beaming ultrasonic energy through an object to be examined. Reflecting means having scatters disposed therein is acoustically coupled to the object opposite the transducer for reflection of ultrasonic energy back through the object. Ultrasonic energy waves reflected from within the reflecting means are received by the transducer where they are converted to electrical signals. Mechanical and/or electronic beam focusing means for focusing within the object, and beam scanning means for scanning the section to be imaged are provided. Signal processing means responsive to the electrical signal output from the transducer functions to process signals received from a range zone within the external reflecting means for generation of an image of a section of the interior of the object. The invention is well suited for the internal examination of body parts such as breasts, testes, and the like.

The invention, together with other objects features and advantages thereof will be more fully understood from a consideration of the following detailed description of certain embodiments thereof taken in connection with the accompanying drawings. It here will be understood that the drawings are for purposes of illustration only, the invention not being limited to the specific embodiments disclosed therein.

BRIEF DESCRIPTION OF THE DRAWINGS

In the drawings, wherein like reference characters refer to the same parts in the several views.

DETAILED DESCRIPTION OF THE INVENTION

Figure 1:
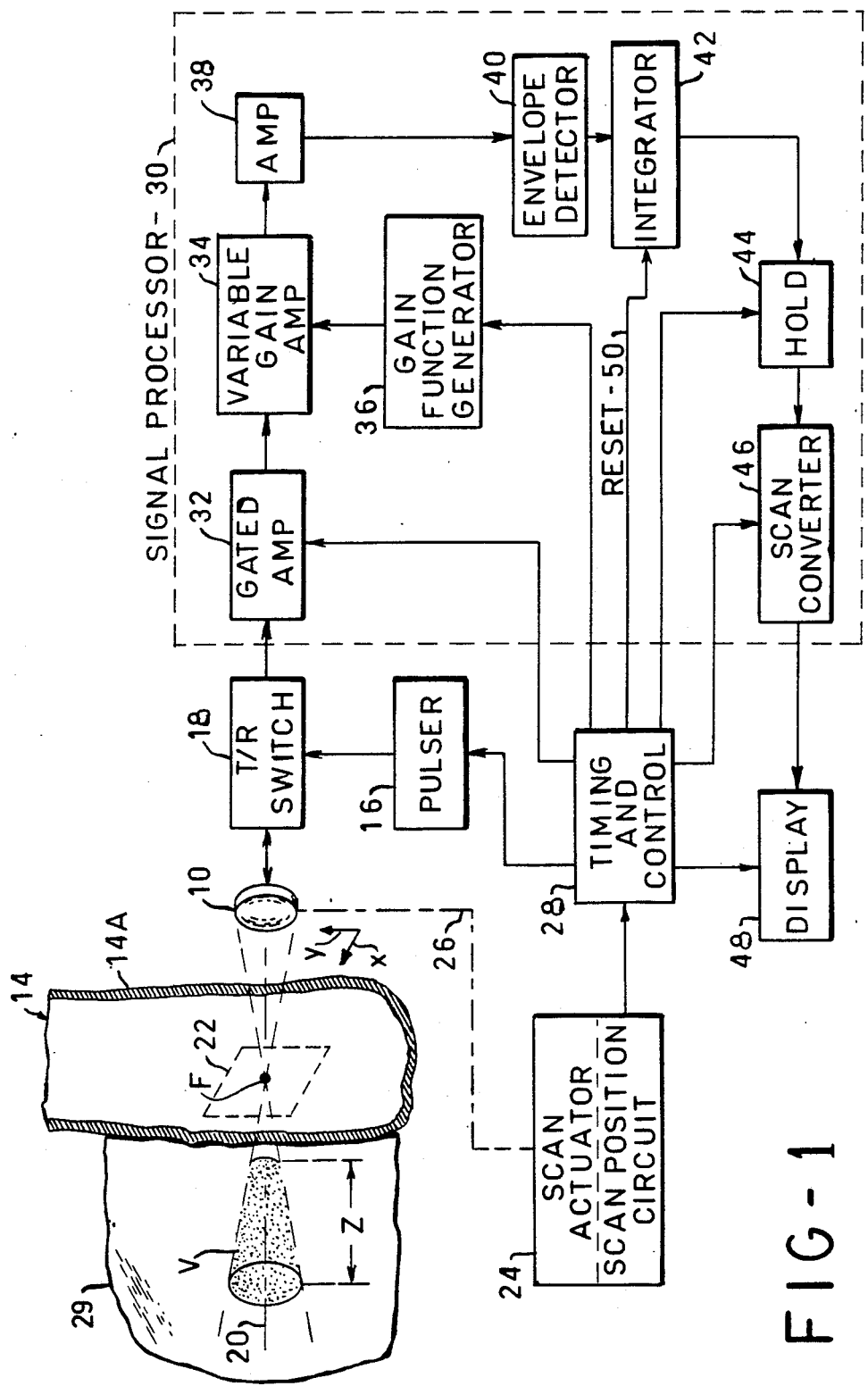
FIG. 1 is a block diagram showing an ultrasonic imaging systems embodying the present invention.

Reference first is made to FIG. 1 wherein there is shown an ultrasonic imaging system comprising a transducer 10 which, in the illustrated arrangement is used for transmitting and receiving ultrasonic pulse signals. For purposes of illustration, a curved focusing transducer is shown. Ultrasonic compressional waves generated by focusing transducer 10 are coupled through a suitable acoustic transmission medium such as water, not shown, to the subject 14 under investigation and are focused within the subject. As will become apparent herein below, the system of this invention is well adapted for ultrasonic imaging of living body soft tissue such as breasts, testes, or the like, through which transmitted and echo signals may completely pass without excessive attenuation or reflection.

In place of the focusing transducer, it will be apparent that other acoustical focusing means such as an acoustic lens, a curved acoustical mirror, or the like, may be employed. Also, electronic focusing may be employed in lieu of, or in addition to, acoustical focusing means. Also, as will become apparent hereinbelow, although focusing during both transmitting and receiving operatons is preferred, focusing only during receiving operation or only during transmitting operation is required.

The transmitting portion of the system includes pulser 16 for recurrent generation of high frequency energy pulses which are supplied through transmit-receive switch 18 to transducer 10 for pulse generation of ultrasonic waves which are focused at focal point F within the subject 14. Typically, an operating frequency of from, say, 1 MHz to 10 MHz may be employed. The ultrasonic beam axis is identified by reference numeral 20 and, in the illustrated embodiment of the invention, a C-scan image of plane 22 normal to axis 20 is obtained by movement of the focal point F in the plane to scan the same. The transducer 10 and associated focusing lens 12 are scanned in the x and y directions shown in FIG. 1 by scan actuator 24 connected thereto through mechanical linkage 26. The scanning mechanism 24 includes a scan position information circuit having an output connected to timing and control unit 28 which, in turn, has outputs for synchronizing the transmitting, receiving, and display scanning operations.

In accordance with the present invention, reflecting means 29 is acoustically coupled to the body part 14 opposite the transmitting transducer 10. The reflecting means may comprise, for example, a gel with scatterers or discontinuities substantially uniformly distributed therein, a liquid-filled member such as a water-filled sponge, a liquid-filled plastic pouch with scatterers disbursed therein, or the like. Gels containing scatterers are shown in P. D. Edmonds, et al., "A Human Abdominal tissue Phantom", Ultrasonic Tissue Characterization II, M. Linzer, ed., Nat. Bureau of Standards, Spec. Publ. 525 (1977) and a liquid-filled pouch with scatterers in the liquid is shown in J. C. Macado, et al., "Acoustic wave propagation in randomly distributed spherical particles". J. Acoust. Soc. Amer., 74(5), 1983. Reflecting means 29 may have scatter, attenuation and velocity characteristics which are similar to that of soft tissue of subject 14, but preferably is non-biological in nature. Ultrasonic energy from transducer 10 enters the body part through a layer of skin 14A, passes completely through the body part to exit therefrom through skin at the opposite side thereof. From the body part, the transmitted beam enters the reflecting means 29 and is reflected from scatterers or discontinuities included therein.

Reflected ultrasonic signals from scatterers, or discontinuities, within reflecting means 29 return through the body part 14. Reflected signals received by transducer 10 are converted to electrical signals and supplied through transmit-receive switch 18 to a signal receiver, or processor, 30 which, for purposes of illustration, includes a gated amplifier 32. A preamplifier, not shown, may be included in the connection of the received signals to amplifier 32. A time gate signal is supplied to gated amplifier 32 from timing and control unit 28 for control of the receiving operation. In the illustrated embodiment, the receiver is gated on for processing of echo signals received from a volume V within a range zone Z located within reflecting means 29 behind the focal plane 22 and focal point F which, as noted above, are located within the subject 14. The illustrated range zone Z is located entirely within the reflecting means 29 adjacent the interface between the subject 14 and reflecting means. In the illustrated embodiment, only reflected signals received from within range zone Z are processed by signal processor 30. Obviously, echo signals received from different depths and/or range zones may be processed by means, not shown. Also, the range zone Z may extend across the interface between the subject 14 and reflecting means 29, if desired.

Since return signals are received from a range of distances, Z, received signals from gated amplifier 32 are amplified by variable gain amplifier 34, the gain of which is time varied in accordance with the output from a gain function generator 36. The timing of the operation of gain function generator 36 is under control of timing and control unit 28. The gain of amplifier 34 is increased in proportion to range so as to offset the loss of signal caused by acoustic absorption within the subject 14 and reflecting means 29, If desired, a time gain function which approximates the condition wherein reflected waves passing through the focal point F from volume V are of equal amplitude may be employed.

From variable gain amplifier 34, received signals are shown coupled to amplifier 38 having a desired gain function. For example, amplifier 38 may comprise a linear amplifier or a non-linear amplifier.

The amplifier 38 output is detected as by envelope detector 40 comprising, for example, a full wave rectifier with low pass filter means and having as an output a signal which is proportional to the envelope of the high frequency signal output from amplfier 38. The detector output is supplied to an integrator 42 for time integration thereof during the period that signals are received from within range zone Z. After each integrating operation, the integrator output is supplied to a hold circuit 44 from whence it may be transferred to a scan converter 46 and thence to visual display means 48, such as a cathode ray tube, under control of timing and control unit 28. At the end of the receiving operation, after transfer of the integrator output to hold circuit 44, the integrator 42 is reset by application of a reset signal thereto over line 50 from timing and control unit 28 in preparation for the next transmit/receive cycle. In the FIG. 1 embodiment, information for display of a single pixel is obtained for each transmit/receive cycle.

Figure 2:
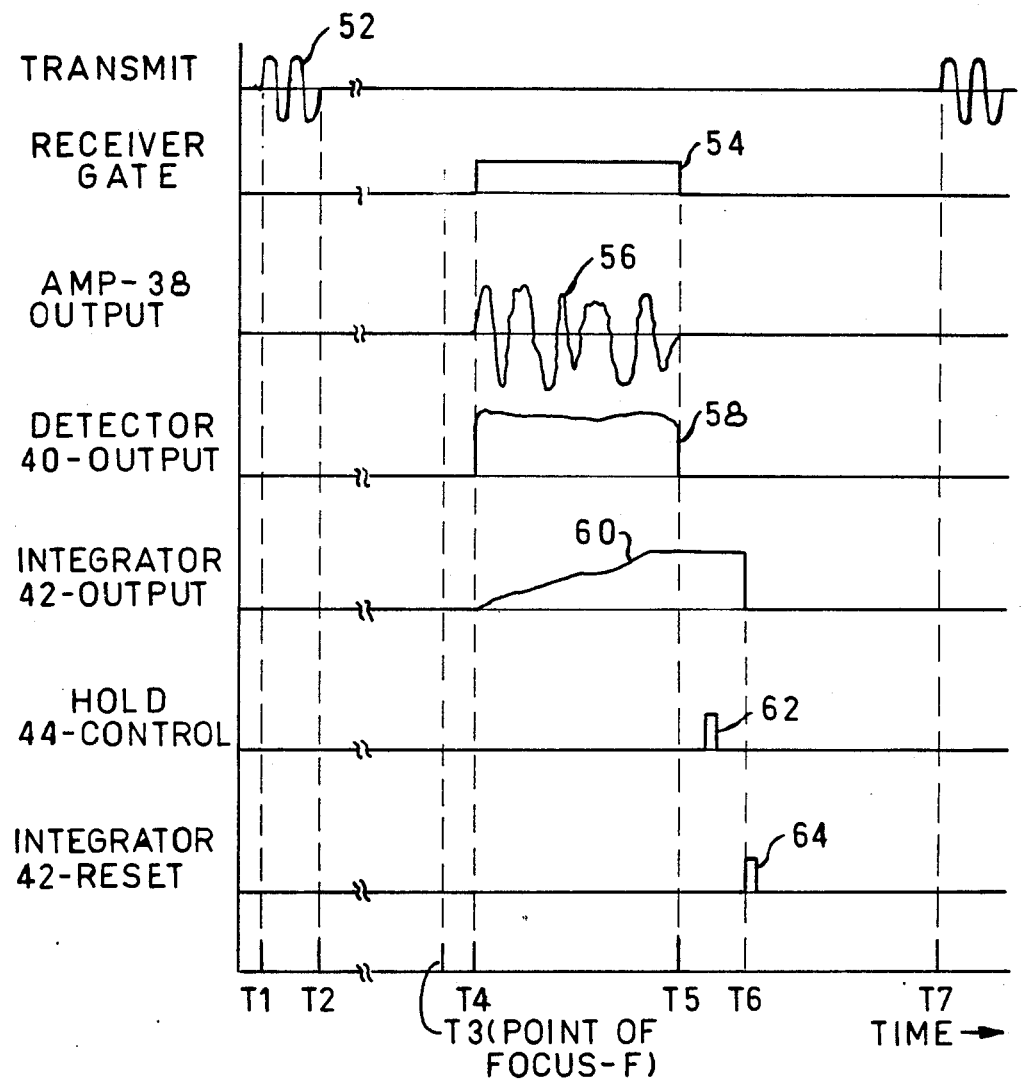
FIG. 2 is a timing diagram for use in explaining operation of the system shown in FIG. 1.

Although the operation of the ultrasonic imaging system of FIG. 1 is believed to be apparent from the above description, a brief description thereof with reference to the timing diagram of FIG. 2 now will be made. The focusing transducer 10 is moved across the subject 14 in the x and y directions by scanning mechanisms 24. A scan position signal is produced by the scan position circuit associated with the scanning mechanism and supplied to the timing and control unit 28 from which control signals for timing operation of the transmitter, receiver, and display means are obtained, During the transmit period, between times T1 and T2, ultrasonic waves are generated by transducer 10 which is energized by the output from pulser 16. In FIG. 2, transmitter pulses are shown at 52. The ultrasonic wave pulse from focusing transducer 10 travels through the subject 14 into reflecting means 29. At time T3 echo signals reflected from focal point F are received by the transducer 10. After a time delay between times T2 and T4, the receiver is gated on by receiver gate signal 54 supplied to gated amplifier 32 from the timing and control unit for processing echo signals received from range zone Z within reflecting means 29. The time gated received signal output from amplifier 38 is shown at 56 of FIG. 2. The received signal is detected by detector 40 having an output 58. The detected signal is integrated by integrator 42, the integrator output being shown at 60 in FIG. 2. After the receiver is gated off, at time T5, the integrator output is transferred to hold circuit 44 under control of hold control signal 62. Following such transfer, at time T6, the integrator 42 is reset by reset signal 64. The next transmit-receive cycle starts at time T7 with the transmission of another insonifying pulse 52.

From the above, it will be apparent that all of the transmitted energy, save that scattered and absorbed before the focal point F, is transmitted through the point of focus. It then passes out of the subject 14 into reflecting means 29. Once past the focal point, the energy spreads out into a cone shape, and is scattered by inhomogeneities of the reflecting means within the generally conical volume V. If the discontinuities, or scatters, within reflecting means 29 are substantially uniformly distributed, then volume V therein provides an effectie extended incoherent insonification source. It will provide most effective insonification if the waves reflected through the focus F from each lamina of range zone are of substantially the same amplitude, and this condition is approximated by time-gain correction of the receiver as noted above. However, if the signal to noise ratio at increased depths is too low, then a time-gain correction which provides for an improved signal to noise ratio at such depths may be employed.

Scattered waves are received by the transducer 10, but those passing through focus F have the most influence on the signal generated by the receiving transducer. Where focusing during both transmission and reception is employed, as in the arrangement of FIG. 1, the received waves pass through the focus twice, and their amplitude is strongly influenced by attenuation within it. With the present invention transmission-type images by backscatter may be obtained of focal planes 22 within the subject which are adjacent the skin 14A where the transmitted signal exits the subject and enters reflecting means 29. Operation wherein backscatter is obtained from scatters within the subject itself is shown in above-mentioned parent application Ser. No. 715,199.

Figure 3:
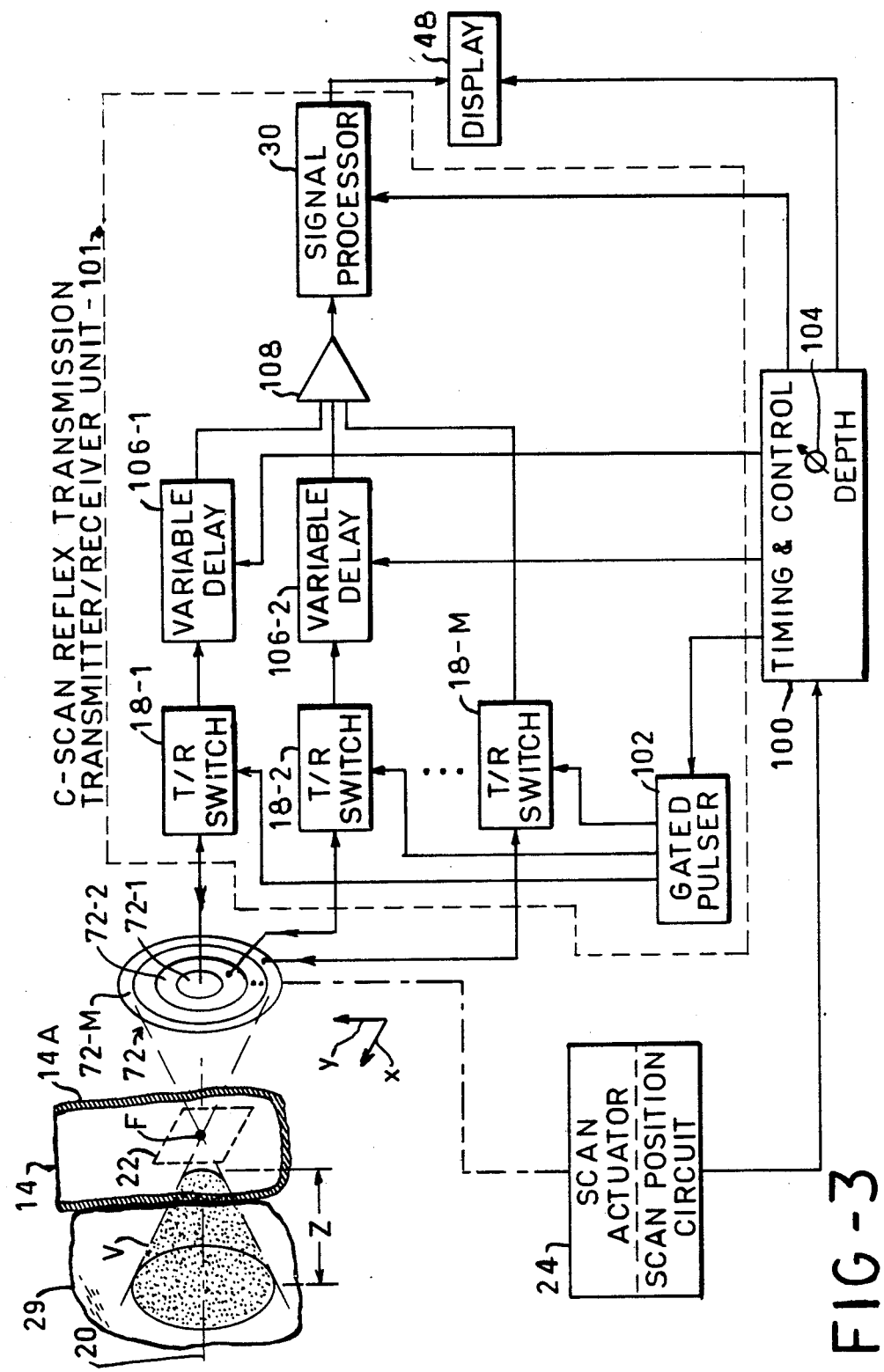
FIG. 3 is a block diagram showing a modified form of ultrasonic imaging system embodying this invention for use in C-scan imaging of the object at selected planes.

Reference now is made to FIG. 3 of the drawings wherein a modified form of this invention is shown which is adapted to obtain C-scan images at selected focal planes. The system illustrated in FIG. 3 includes an annular transducer array 72 which is used for pulse insonification and reception. For purposes of illustration only, a transducer which includes a central circular electrode 72-1 and concentrically disposed annular electrodes 72-2 through 72-M is shown.

A scan actuator and scan position circuit 24 mechanically moves the transducer in two dimensions along the x and y axes, and supplies position signals to timing and control unit 100. The transmitter/receiver unit 101 includes a gated pulser 102 which is connected to the array elements through transmit/receive switches 18-1 through 18-M. Pulser 102 operates at a single center frequency, and timing of the gating of the output therefrom to the elements of the transducer array provides for focusing of the transmitted ultrasonic pusles at a selected depth under control of depth control 104 at timing and control unit 100. In FIG. 3, the transducer is shown focused at focal point F within a subject 14.

In accordance with the invention, reflecting means 29 is acoustically coupled to the subject 14 opposite transducer array 72, whereby the transmitted pulses pass through the subject and into the reflecting means. As noted above, the range zone Z from which echo signals are processed may extend across the interface between the subject 14 and reflecting means 29, and in FIG. 3 such a situation is illustrated. There, the range zone Z is seen to extend from a location in the subject opposite the focal point F to a location in the reflecting means 29.

Electrical signals produced by echo waves at the transducer elements are supplied to summing amplifier 108. Variable delay means are included in the connection of all but the outer annular element 72-M of the transducer array to the summing amplifier for focusing of the received signal at substantially the same focal point at which the transmitted pulse is focused under control of depth control 104. In FIG. 3 two of the variable delay means 106-1 and 106-2 for connection of transducer elements 72-1 and 72-2, respectively, to the summing amplifier are shown. Signal processor 30 of the same type shown in FIG. 1 and described above processes the signal to provide a C-scan image at display unit 48. On-off gating of the gated amplifier included in the signal processor also is under control of depth control 104 for controlling the range zone Z from which echo signals are processed in association with the transmit and receive focal points established by the setting of depth control 104. In this case, echo signals reflected from scatterers, or discontinuities, in both the subject and the reflecting means, within volume V which is intersected by the interface therebetween, are processed for obtaining an image of focal plane 22 within the subject.

The invention having been described in detail in accordance with requirements of the patent statutes, numerous other changes ad modifications will suggest themselves to those skilled in this art. However, all such modifications include the use of reflecting means having discontinuities or scatterers distributed therein acoustically coupled to the subject opposite the ultrasonic probe, from which discontinuities or scatterers echo signals are received during at least a portion of the receiving operation.

Reflecting means of this type may be used in conjunction with a wide variety of reflex transmission imaging systems and methods. For example, reflecting means may be used with a system for obtaining three dimensional images of a portion of the interior of a subject. With such systems, information for imaging at a plurality of different planes is obtained. For simultaneous display, signals representative of different planes may be displayed in separate color for distinguishing therebetween at a display. Alternatively, signals may be combined to form stereoptic pairs, or otherwise combined, or displayed separately.

Also B-scan images may be produced by displaying, as a function of range, the integrated signal from a range zone beyond each point in the B-scan range, at least some of which signals are echoed from external reflecting means acoustically coupled to the subject. This requires both dynamic focus and a continuous time shifting of the zone of integration, a process that is easily implemented in the digital domain. For improved resolution, a compound scan is employed therewith. In any event some, if not all pixel information for the display, whether C-scan or B-scan, is obtained from a range zone, or portion of a range zone, inside the reflecting means acoustically coupled to the subject.

Reflex transmission imaging systems may be combined with other systems such as a conventional B-scan system wherein information for a B-scan display is obtained from reflections from within the subject and information for the display of the reflex transmission image is obtained completely, or partially, from scatterers included in reflecting means acoustically coupled to the subject.

Also, the present invention may be used in reflex transmission imaging systems which employ different scanning patterns, different scanning means and/or different types of ultrasonic tranducers. For example, a linear transducer array may be used in place of a focused transducer for linear-linear, linear-sector, or like type scanning patterns. Also, either a focused transducer (such as shown in FIG. 1) or a phased transducer array (such as shown in FIG. 3) may be used with substantially any desired scanning pattern such as linear-linear, linear-sector, sector-sector, spiral, star, or the like.

Digital signal processing methods rather than analog ones shown and described herein may be employed in the practice of this invention. Further, it will be apparent that receiver operations are well adapted for performance by software in a suitably programmed computer, or computers. Also, separate transmitting and receiving transducers which are closely located may be employed, if desired. Obviously, gating of the receiver, or signal processor, at points other than at a gated amplifier at the receiver input is contemplated. For example, gated integrators may be employed. Furthermore, it will be apparent that a chirped signal, or otherwise coded signal source, may be employed to generate a chirped or otherwise coded ultrasonic wave, together with a receiver for processing the chirped or coded echo signals such that the portion of received signal being detected and integrated from a range zone at least partially located in the reflecting means externally coupled to the subject represents information from a focal point within the subject.

Further, continuous rather than pulse operation of the novel imaging system may be employed by using a continuously variable frequency, or otherwise coded, source and associated receiver. Obviously, a conventional C-scan image may be obtained at the same time a reflex transmission C-scan image is obtained by simply processing those signals reflected from scatterers at the focal point, in a conventional manner, then processing those signals obtained from a range zone within the reflecting means, in a manner described herein.

Additionally, the invention is not limited to use of the above-described reflecting means or to reflecting means wherein the scatterers or discontinuities are substantially uniformly distributed. For example, reflecting means wherein the density of scatterers or discontinuities varies in, for example, the front to back direction thereof may be employed. Also, other reflecting means may be employed in the operation of this invention. It is intended that the above and other such changes and modifications shall fall within the spirit and scope of the invention as defined in the appended claims.

I claim:

1. In an ultrasonic imaging method for imaging the interior of objects such as body parts, the steps comprising
   acoustically coupling reflecting means having scatterers therein to an object,
   transmitting an ultrasonic beam through a portion of the object into said reflecting means and receiving echos reflected from scatterers within said reflecting means, and
   processing echos received from a range zone within said reflecting means to form data for a display of a portion of the interior of the object through which received echo signals pass.

2. In an ultrasonic imaging system as defined in claim 1 including focusing the ultrasonic beam at a focal point within said object.

3. In a reflex transmission ultrasonic imaging method for non-invasive examination of the interior of objects such as parts of a subject's body, the steps comprising
   acoustically coupling ultrasonic transducer means to a body part,
   focusing said ultrasonic transducer means at a focal point within said body part,
   acoustically coupling reflecting means having scatterers distributed therein to said body part opposite said transducer means,
   energizing said ultrasonic transducer means for beaming ultrasonic energy through said body part and into said reflecting means,
   receiving by said ultrasonic transducer means echo signals from scatterers within said reflecting means, which echo signals return through said body part, and
   processing echo signals received from scatterers within said reflecting means over a range of depths therewithin to form data for a display of a portion of the interior of said body part at which said transducer means is focused.

4. In a reflex transmission ultrasonic imaging method as defined in claim 3 wherein focusing of said ultrasonic transducer is provided during energization thereof.

5. In a reflex transmission ultrasonic imaging method as defined in claim 3 wherein focusing of said ultrasonic transducer is provided during receiving operation thereof.

6. In a reflex transmission ultrasonic imaging method as defined in claim 3 wherein focusing of said ultrasonic transducer is provided both during energization thereof and during receiving operation thereof.

7. In a reflex transmission ultrasonic imaging method as defined in claim 3 wherein echo signals received by said ultrasonic transducer means are converted to electrical signals, said processing step including
   detecting electrical signals from said transducer means,
   integrating detected signals received over a time period that echo signals are received from said range of depths within said reflecting means, the integrated signal being related to attenuation at the focal point within said body part, and
   using the integrated signal to establish a pixel of a display.

8. Ultrasonic apparatus for examining the interior of an object such as a subject's body part, said apparatus comprising
   ultrasonic reflecting means having scatterers distributed therewithin,
   means for acoustically coupling said reflecting means to an object under examination,
   ultrasonic transducer means for transmitting ultrasonic energy through said object into said reflecting means and for receiving echo signals from scatterers within said reflecting means,
   means for focusing said ultrasonic transducer means at a focal point within said object, and
   processing means for processing echo signals received by said ultrasonic transducer means from over a range of depths within the reflecting means to form data for a display of a portion of the interior of said object.

9. Ultrasonic apparatus as defined in claim 8 wherein said reflecting means is non-biological.

10. Ultrasonic apparatus as defined in claim 9 wherein said reflecting means comprises a liquid-filled sponge.

11. Ultrasonic apparatus as defined in claim 9 wherein said reflecting means comprises a gel with substantially uniformly distributed scatterers therein.

12. Ultrasonic apparatus as defined in claim 9 wherein said reflecting means comprises a liquid-filled pouch with scatterers dispersed therein.

13. Ultrasonic apparatus as defined in claim 8 wherein said processing means includes integrating means for integrating echo signals received from over said range of depths.

14. Ultrasonic apparatus as defined in claim 8 wherein said processing means includes means for processing echo signals received from a range zone which extends across the interface between said object and reflecting means.

15. In a reflex transmission ultrasonic imaging system for imaging a section of the interior of a subject's body, the combination including
   ultrasonic transducer means, transmitter means for energizing the transducer means for beaming ultrasonic energy waves through a subject's body part, reflecting means having scatterers disposed therein acoustically coupled to the body part for reflecting ultrasonic energy waves which have passed through said body part back through said body part, said transducer means receiving energy waves reflected from scatterers within the reflecting means and converting the same to electrical signals, receiver means responsive to electrical signals from said transducer means for processing signals derived from a range zone within said reflecting means, and focusing means for focusing the transducer means at a focal point within the subject's body part, the amplitude of ultrasonic energy waves reflected from said range zone within said reflecting means being substantially dependent upon attenuation at the focal point within the object.

16. In a reflex transmission ultrasonic imaging system as defined in claim 15 wherein said receiver means includes means for detecting electrical signals from said transducer means, means for integrating detected signals over a time period that reflected signals are received from said range zone, and means for constructing an ultrasonic image employing the output from said integrating means.

17. In a reflex transmission ultrasonic imaging system as defined in claim 16 wherein a C-scan image is constructed by the constructing means.

* * * * *